US006245403B1

(12) United States Patent
Spahni et al.

(10) Patent No.: US 6,245,403 B1
(45) Date of Patent: Jun. 12, 2001

(54) WRITABLE AND ERASABLE HIGH-DENSITY OPTICAL STORAGE MEDIA

(75) Inventors: Heinz Spahni, Frenkendorf (CH); Jin Mizuguchi, Yokohama (JP); Beat Schmidhalter, Giffers (CH); Annemarie Wolleb, Marly (CH); Jean-Luc Budry, Clarens (CH); Gérald Giller, Bulle (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/069,266

(22) Filed: Apr. 29, 1998

(30) Foreign Application Priority Data

Apr. 29, 1997 (CH) ...................................... 997/97

(51) Int. Cl.$^7$ ...................................... B32B 3/02
(52) U.S. Cl. ...................... 428/64.1; 428/64.2; 428/64.4; 428/64.8; 428/913; 430/270.14; 430/495.1; 430/945; 369/283; 369/288
(58) Field of Search ................................ 428/64.1, 64.2, 428/64.4, 64.8, 913; 430/270.14, 945, 495.1; 369/283, 288

(56) References Cited

U.S. PATENT DOCUMENTS

| | | | |
|---|---|---|---|
| 4,443,532 | 4/1984 | Joy et al. | 430/270 |
| 4,812,352 | 3/1989 | Debe et al. | 428/142 |
| 4,937,164 | 6/1990 | Duff et al. | 430/58 |
| 5,319,083 | 6/1994 | Tröster | 546/37 |
| 5,354,869 | 10/1994 | Langhaks et al. | 548/453 |

FOREIGN PATENT DOCUMENTS

| | | |
|---|---|---|
| 38 42 856 | 6/1990 | (DE) . |
| 10-6645 | 1/1998 | (JP) . |

OTHER PUBLICATIONS

Spores, Applied Optics, vol. 26/7, pp. 1240–1245 (1987).
Gregg, J. Phys. Chem., vol. 100, pp. 852–859 (1996).
Okuda et al., J. of Non–Crystalline Solids 97 & 98, pp. 1351–1354 (1987).
Optical Recording, A. B. Marchant, Addison–Wesley Publishing Co., Chapter 4, pp. 67–98 (1990).
Suzuki, Oyu Butsuri, vol. 64, pp. 208–219 (1995).
Graser, et al., Liebigs Ann. Chem., pp. 483–494, vol. 1984, (1984).
Nagao. Y. et al. "Synthesis and properties of N, N'–unsymmetrical dialkyl–3,4:9,10–Perylenebis(dicarboximide)S" Dyes and Pigments, vol. 6, No. 4, 1985, pp. 303–311.
Chemical Abstracts, vol. 110, No. 13, Mar. 27,1989, Abst. No. 114711b, "Anion Radical of Perylenetetracarboxylic dianhydride and diimides" pp. 681.

Patent abstracts of Japan vol. 098, No. 005, Apr. 30,1998 & JP 10006645 Jan. 13,1998.

Derwent Abst. 90–194391 [26] of DE 38 42 856.

Primary Examiner—Elizabeth Evans
(74) Attorney, Agent, or Firm—David R. Crichton; Kevin T. Mansfield

(57) ABSTRACT

The invention relates to an optical storage medium comprising a substrate and a storage layer, wherein the storage layer comprises a compound of the formula (I) or (II)

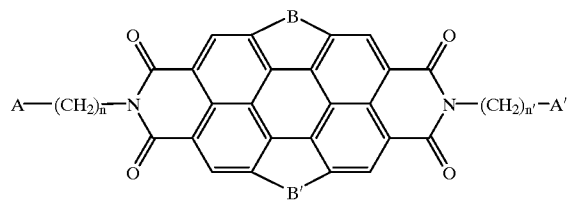

(I)

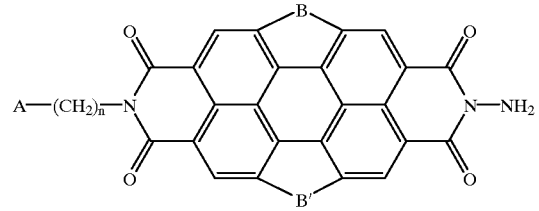

(II)

in which A and A', independently of one another, are unsubstituted or mono- or di-halo-, -hydroxy-, —$C_1$–$C_6$alkyl-, —$C_1$–$C_6$alkoxy-, -cyano- or -nitro- substituted phenyl, pyridyl, pyrrolyl, imidazolyl, furyl or thienyl, which can, if desired, be fused to a benzene ring, are halide, tetrafluoroborate or unsubstituted or with one or more halogen substituted $C_1$–$C_6$alkane-sulfonate, benzenesulfonate, $C_1$–$C_6$alkylbenzenesulfonate, $C_1$–$C_6$alkylsulfate or di-$C_1$–$C_6$alkyl-phosphonate of N—$C_1$–$C_6$alkyl-pyridiniumyl, or are unsubstituted or mono- or di-hydroxy-substituted $C_2$–$C_6$alkyl or $C_2$–$C_6$alkenyl, whose chain may be uninterrupted or interrupted by one or two oxygen atoms, B and B', independently of one another, are 2 H, S, $S_2$ or $SO_2$, and n and n', independently of one another, are each a number from 1 to 4. The invention also relates to a process for the optical writing, storage, reading, modification or erasing of data at a wavelength of from 400 to 700 nm using a novel recording medium, to an optical recorder for the optical writing, modification or erasing of data using only continuous laser radiation or only modulated laser radiation, to a process for converting a compound of the formula (I) or (II) from a black form into a red form by mechanical force, and to new compounds of the formula (I) or (II).

30 Claims, No Drawings

WRITABLE AND ERASABLE HIGH-DENSITY OPTICAL STORAGE MEDIA

The invention relates to the field of optical data storage on writable and erasable high-density storage media, where the bits of information differ through the optical properties at the written and unwritten pits. The novel storage media contain, as storage elements, certain perylene pigments and can be used, for example, as disks having a diameter of 120 or 80 mm in the multi-rewritable DVD-RAM format.

The invention likewise relates to a process for the optical recording, storage, reproduction, modification or erasure of data at a wavelength of from 400 to 700 nm in which a novel storage medium is used.

In the multimedia age, the storage capacity of conventional CD disks is no longer sufficient [Oyo Butsuri 64, 208–219 (1995)]. Attempts are therefore being made to replace the CD format by the DVD format ("DVD" stands for "digital video disk" or "digital versatile disk"). The aim is a storage capacity of at least 4.7 Gbyte. However, DVD disks having a capacity of 4.7 Gbyte can only be produced by series embossing using a master (DVD-Video, DVD-Audio, DVD-ROM), and individually are neither writable nor erasable.

WO 90/01480 describes the use of fluorescent diketopyrrolopyrrole and perylenetetracarboxylic diamide dyes as optical data storage elements. These dyes can initially be in the form of crystals with a uniform size of from 0.1 to 200 μm and can be converted from a non-fluorescent modification into a fluorescent modification by irradiation with a laser beam. If the dyes are used together with a thermally stable auxiliary substance having a melting point of from 170 to 190° C., the written fluorescent data store can be erased again by heating to above 220° C. However, the erasing speed is very slow; in addition, these systems have an unsatisfactory life, and detection of the fluorescence is technically very complex.

U.S. Pat. No. 4,812,352 describes discontinuous microstructures of N,N'-di(3,5-xylyl)perylene-3,4:9,10-bis(dicarboximide) in the form of a coating on a substrate. Although it is claimed that they can be used for data storage, specific examples of this application are not disclosed. If data storage should nevertheless succeed, this would be an irreversible process, since the microstructures grow only very slowly in a high vacuum, so that they are impossible to regenerate reasonably easily (for example in a writing device). In addition, these microstructures have a length of 1.5 μm and have a low refractive index, so that they are unsuitable for the high capacity and high resolution desired.

Applied optics [26/7, 1240–5 (1987)] describes films comprising anthraquinone dyes which melt without decomposing and can be converted, using a modulated krypton ion laser having a wavelength of 647.1 nm, from an amorphous phase into a crystalline phase or vice versa, depending on the pulse length. However, the erasing speed, in the region of milliseconds, is much too slow for practical use.

However, the dye systems only meet the requirements of DVD-R and DVD-RAM to an unsatisfactory extent, in particular with respect to the high storage density and the erasing speed. In addition, dyes, in contrast to pigments, have poor light stability; in addition, heating, as is repeatedly necessary in DVD-RAM, causes dyes to decompose or diffuse into the adjacent high-molecular-weight medium, forming "holes". Such systems therefore have a short life. Furthermore, crystallization is, in spite of the use of nucleating layers, too slow to enable targeted, selective erasure of individual pits or areas on the storage medium at normal recording or reading speeds.

Writable and erasable storage media comprising eutectic mixtures of Ga—Se—Te are disclosed in Journal of Non-Crystalline Solids 97&98, 1351–1354 (1987). The storage layer of these media can be converted from a crystalline phase into an amorphous phase and vice versa using a semiconductor laser having a wavelength of 830 nm, with an erasure time of 1 μs being achievable under optimum conditions. The use of more recent compact, high-power red diode lasers, which emit in the range from 630 to 690 nm, in principle enables an improvement in the data packing density by allowing a reduction in the track separation (distance between 2 turns of the data track) and the size of the marks (pits).

However, the desired high storage density of 4.7 Gbyte per 120 mm disk side nevertheless cannot be achieved using these storage media, but instead only a storage density of 2.6 Gbyte. In addition, the precise composition of the eutectic mixture is extremely important, so that the production of such media is difficult and expensive. Moreover, mass consumer products containing Ga, Se and/or Te are very undesirable for ecotoxicological reasons. Also, systems based on material flow exhibit non-negligible phase separation on ageing [Optical Recording, A. B. Marchant, Addison-Wesley Publishing Company, 87 (1990)], so that their durability and the long-term security of the data written thereon is not guaranteed.

Surprisingly, it has now been found that writable and erasable high-density optical data storage media with a high writing and erasing speed and improved properties are obtained if certain perylene pigments are used in the storage layer. These media are suitable for use as DVD-R and in particular also as DVD-RAM.

The invention relates to an optical storage medium comprising a substrate and a storage layer, wherein the storage layer comprises a compound of the formula (I) or (II)

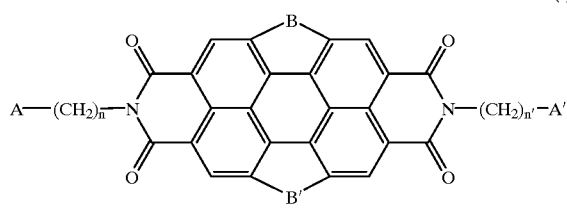

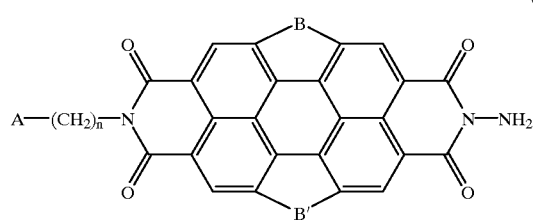

in which A and A', independently of one another, are unsubstituted or mono- or di-halo-, -hydroxy-, —$C_1$–$C_6$alkyl-, —$C_1$–$C_6$alkoxy-, -cyano- or -nitro-substituted phenyl, pyridyl, pyrrolyl, imidazolyl, furyl or thienyl, which can, if desired, be fused to a benzene ring, are halide, tetrafluoroborate or unsubstituted or with one or more halogen substituted $C_1$–$C_6$alkane-sulfonate, benzenesulfonate, $C_1$–$C_6$alkylbenzenesulfonate, $C_1$–$C_6$alkylsulfate or di-$C_1$–$C_6$alkyl-phosphonate of N-$C_1$–$C_6$alkyl-pyridiniumyl, or are unsubstituted or mono- or di-hydroxy-substituted $C_2$–$C_6$alkyl or $C_2$–$C_6$alkenyl, whose chain may be uninterrupted or interrupted by one or two oxygen atoms, B and B', independently of one another, are 2 H, S, $S_2$ or $SO_2$, and n and n', independently of one another, are each a number from 1 to 4.

A and A' are preferably phenyl or $C_2$–$C_6$alkyl. Any substituents of phenyl are preferably hydroxyl, halogen, methyl or methoxy. $C_2$–$C_6$Alkyl is preferably unsubstituted or substituted with one hydroxy group.

B and B' are preferably each 2 H.

n and n' are preferably each the number 1 or 2, and are particularly preferably both the number 2.

Halogen is chlorine, bromine, fluorine or iodine, preferably chlorine or bromine.

Alkyl or alkenyl, for example $C_1$–$C_6$alkyl or $C_2$–$C_6$alkenyl, can be straight-chain, branched or cyclic. $C_1$–$C_6$alkyl is therefore, for example, methyl, ethyl, n-propyl, isopropyl, n-butyl, sec-butyl, isobutyl, tert-butyl, cyclobutyl, n-pentyl, 2-pentyl, 3-pentyl, 2,2-dimethylpropyl, cyclopentyl, n-hexyl, 2-ethylbutyl or cyclohexyl.

$C_1$–$C_6$Alkanesulfonate is preferably methanesulfonate, ethanesulfonate or trifluoromethane-sulfonate, most preferably methanesulfonate. $C_1$–$C_6$Alkyl in $C_1$–$C_6$alkylbenzenesulfonate, $C_1$–$C_6$alkylsulfate or di-$C_1$–$C_6$alkyl-phosphonate is preferably methyl, ethyl or trifluoromethyl, most preferably methyl. $C_1$–$C_6$Alkyl in N—$C_1$–$C_6$alkyl-pyridiniumyl is preferably $C_1$–$C_4$alkyl, most preferably methyl.

$C_2$–$C_6$Alkenyl is $C_2$–$C_6$alkyl which is mono- or polyunsaturated, where two or more double bonds, if present, can be isolated or conjugated, for example vinyl, allyl, 2-propen-2-yl, 2-buten-1-yl, 3-buten-1-yl, 1,3-butadien-2-yl, 2-cyclobuten-1-yl, 2-penten-1-yl, 3-penten-2-yl, 2-methyl-1-buten-3-yl, 2-methyl-3-buten-2-yl, 3-methyl-2-buten-1-yl, 1,4-pentadien-3-yl, 2-cyclopenten-1-yl, 2-cyclohexen-1-yl, 3-cyclohexen-1-yl or 2,4-cyclohexadien-1-yl.

$C_1$–$C_6$Alkyl which is interrupted by oxygen is, for example, 3-oxapentyl, 2-oxacyclopentyl, 2-oxa-3-methylcyclopentyl, 3-oxahexyl or 2,5-dioxacyclohexyl.

Some compounds of the formula (I) or (II) are known compounds whose preparation is disclosed, for example, in CH 37 163, CH 618 209, DE 2 612 855, GB1 537 358, U.S. Pat. No. 4,937,164 and U.S. Pat. No. 5,319,083. The other compounds of the formula (I) or (II), which also can be prepared by methods known per se analogously to the known compounds, for example by the methods disclosed in the abovementioned publications or in Dyes and Pigments 4, 71–77 (1983), are however still novel.

The invention relates also to the compounds of the formula (I) or (II), with the exception of all already described compounds of the formula (I) or (II). Known compounds are compounds of the formula (I), wherein B and B' are each 2H and A and A' are each benzyl, 3-fluoro-benzyl, 3-chloro-benzyl, 3-methoxy-benzyl, 2-phenyl-ethyl, 2-(3'-chloro-phenyl)-ethyl, 2-(3'-methyl-phenyl)-ethyl, 2-(4'-methyl-phenyl)-ethyl or 2-(4'-methoxy-phenyl)-ethyl.

Preferred compounds of the formula (I) or (II) are such, in which A and A' are pyridyl or halide, tetrafluoroborate or unsubstituted or with one or more halogen substituted $C_1$–$C_6$alkanesulfonate, benzenesulfonate, $C_1$–$C_6$alkylbenzenesulfonate, $C_1$–$C_6$alkylsulfate or di-$C_1$–$C_6$alkyl-phosphonate of N—$C_1$–$C_6$alkyl-pyridiniumyl. These compounds, particularly the N—$C_1$–$C_6$alkyl-pyridiniumyl salts, can easily be spin-coated.

Also preferred are compounds of the formula (I) or (II), in which A and A' are unsubstituted or mono- or di-hydroxy-substituted $C_2$–$C_6$alkyl or $C_2$–$C_6$alkenyl, whose chain may be uninterrupted or interrupted by one or two oxygen atoms.

Suitable compounds of the formula (I) or (II) are those which occur as a solid in at least 2 forms whose absorptivities k at 650 nm ($k_{650}$) corresponding to the imaginary part of the complex refractive index differ by at least 0.05, preferably by at least 0.1. $k_{650}$ is particularly preferably at least 0.2 in one form and at most 0.15 in the other form.

In general, it can be assumed that of the known crystalline compounds of the formula (I) or (II), those which are referred to as "black" in, for example, the Colour Index or in other publications which disclose their individual structures satisfy the inventive condition $k_{650} \geq 0.2$. In all compounds of the formula (I) or (II), including those which are novel, the solid spectrum can be measured by methods known per se. If the compounds of the formula (I) or (II) according to the invention are obtained from the synthesis in amorphous form, they can be converted into crystalline form by methods which are likewise known per se, for example by treatment with a conventional solvent or vapours thereof, for example for a time of from 10 s to 100 h, depending on the solvent and the solubility, if desired with heating to a temperature of from 30 to 250° C. This method is disclosed, for example, in J. Phys. Chem. 100, 852–859 (1996).

If a solvent is used for the conversion into a crystalline form, it is advantageous to remove it again thereafter, since otherwise the surprising advantages of the novel storage media are not achieved to a fully satisfactory extent. Preference may therefore likewise be given to solvents whose boiling point is low, advantageously $\leq 200°$ C., preferably $\leq 100°$ C.

The compounds of formula (I) or (II) may also be converted to their crystalline form through heating, for example to a temperature of 40 to 160° C., in the absence of a solvent.

Surprisingly, it has been found that the compounds of the formula (I) or (II) according to the invention can be converted from a form having a higher $k_{650}$ into a form having a lower $k_{650}$ by applying a mechanical force, for example by rubbing or pressing. Depending on the compound, the requisite pressure is approximately from $10^0$ to $10^{10}$ g/m$^2$, preferably from about $10^7$ to about $10^9$ g/m$^2$. It should be noted, however, that at high pressures, for example above $10^9$ g/m$^2$, the pressure may also deform the substrate, for example a high-molecular-weight material onto which the compounds of the formula (I) or (II) are coated; this is generally undesired. The invention therefore also relates to a process for converting a compound of the formula (I) or (II) from a form having a higher $k_{650}$ into a form having a lower $k_{650}$ by applying a mechanical force. Generally, the form with higher $k_{650}$ is black or brown and crystalline, and the form with a lower $k_{650}$ is red and amorphous or polycrystalline.

The existence of a "black" crystalline phase can also be deduced from model calculations of the crystal, it being possible to predict the colour in, for example, the method indicated in Liebigs Ann. Chem. 1984, 483–494.

The compounds of the formula (I) or (II) according to the invention have a high refractive index n on the long-wave edge of the absorption band; this refractive index preferably reaches a peak value of from 2 to 3 in the range from 400 to 700 nm, enabling production of a medium of high reflectivity, high sensitivity and good reproduction characteristics in the desired spectral region. n is particularly preferably from 2.0 to 2.5 at 650 nm ($n_{650}$).

The substrate, which functions as support for the layers applied thereto, is advantageously semitransparent (T≦10%) or transparent (T≧90%), preferably transparent. The support can have a thickness of from 0.01 to 10 mm, preferably from 0.1 to 5 mm, particularly preferably from 0.1 to 1 mm, in particular from 0.5 to 0.6 mm. The birefringence is preferably at most 100 nm. The individual optomechanical requirements of the substrate are known to the person skilled in the art.

The storage layer of the novel optical storage medium preferably consists essentially of one or more compounds of the formula (I) or (II), particularly preferably consists essentially of a compound of the formula (I) or (II).

In addition to the substrate and the storage layer, the novel storage medium preferably has an at least partially reflective layer.

The storage layer is preferably applied between the transparent substrate and the reflective layer. The thickness of the storage layer is from 10 to 500 nm, preferably from 20 to 200 nm, particularly preferably from 50 to 100 nm, in particular about 70 nm. The layer thickness is very particularly preferably selected in a known manner, depending on the respective refractive index in the unwritten or in the written state at the reading wavelength, so that a high reflection results in the state containing the compound (I) or (II) in the form having the lower $k_{650}$, due to constructive interference, and, by contrast, a lower reflection results in the state containing the compound (I) or (II) in the form having the higher $k_{650}$, due to absorption.

The reflective layer, which generally has a thickness of from 10 to 150 nm, preferably has high reflectivity (R≦70%) coupled with low transparency (T≦10%).

The uppermost layer depending on the layer structure, for example the reflection layer, is advantageously additionally provided with a protective layer, which can have a thickness of from 0.1 to 1000 µm, preferably from 0.1 to 50 µm, particularly preferably from 0.5 to 15 µm. This protective layer can, if desired, also serve as carrier for an adhesion promoter or itself serve as adhesion promoter onto which a second substrate layer can be applied, preferably with a thickness of from 0.1 to 5 mm, particularly preferably from 0.1 to 1.0 mm, in particular from 0.5 to 0.6 mm, and very particularly preferably made of the same material as the support substrate. In a further embodiment, a storage and reflection layer can likewise be applied to the second substrate layer, so that the storage medium can be written to on both sides.

The reflectivity of the entire storage medium is preferably at least 10%, particularly preferably at least 20%, very particularly preferably at least 45%.

The use of compounds of the formula (I) or (II) gives storage layers having advantageous properties, such as high light stability in daylight at the same time as high sensitivity under laser radiation of high power density, uniform inscription width, and good thermal and storage stability.

Examples of suitable substrates are glasses, minerals, ceramics, thermosets and thermoplastics. Preferred supports are glasses, homopolymers and copolymers. Examples of suitable polymers are thermoplastic polycarbonates, polyamides, polyesters, polyacrylates and polymethacrylates, polyurethanes, polyolefins, polyvinyl chloride, polyvinylidene fluoride, polyimides, thermosetting polyesters and epoxy resins. The substrate can be in pure form or can also include conventional additives, for example UV-absorbers or dyes, as proposed, for example, in JP 04/167 239, as light protection for the storage layer. In the latter case, it may be advantageous for the dye added to the support substrate to have an absorption maximum which is hypsochromically displaced by at least 20 nm, preferably by at least 50 nm, relative to the chromophore of the storage layer.

The substrate is advantageously transparent in at least part of the range from 400 to 700 nm, so that it allows at least 90% of the incident light at the writing or reading wavelength to pass. The substrate has, preferably on the coating side, a spiral guide groove with a depth of from 20 to 500 nm, a width of from 0.2 to 0.8 µm and a separation between 2 turns of from 0.4 to 1.6 µm, particularly preferably having a depth of from 30 to 100 nm, a width of from 0.2 to 0.4 µm and a separation between 2 turns of from 0.6 to 0.9 µm.

Particularly suitable reflective materials for the reflection layer are metals which reflect the laser radiation used for the writing and reading well, for example metals from the third, fourth and fifth main group and the sub-groups of the Periodic Table of the Chemical Elements, such as Al, In, Sn, Pb, Sb, Bi, Cu, Ag, Au, Zn, Cd, Hg, Sc, Y, La, Ti, Zr, Hf, V, Nb, Ta, Cr, Mo, W, Fe, Co, Ni, Ru, Rh, Pd, Os, Ir, Pt and the lanthanide metals Ce, Pr, Nd, Pm, Sm, Eu, Gd, Tb, Dy, Ho, Er, Tm, Yb and Lu, and their alloys. Preference is given to a reflection layer made from Al, Ag, Cu, Au or their alloys for reasons of their high reflectivity and ease of production. Suitable materials for a partially reflective layer are preferably Al, Au, Si/C, and Si/N, and suitable materials for a transparent layer are preferably $SiO_2$, $TiO_2$, $TiO_2/SiO_2$, $Al_2O_3$, ZnS and $ZnS/SiO_2$. The structure and use of such materials are known to the person skilled in the art.

Suitable materials for the protective layer are principally plastics applied in a thin layer to the support or to the uppermost layer either directly or with the aid of adhesion layers. It is advantageous to select mechanically and thermally stable plastics having good surface properties, which may also be modified, for example printed. The plastics can be either thermosetting or thermoplastic. Preference is given to radiation-cured (for example by UV radiation) protective layers, which are particularly simple and economic to produce. A large number of radiation-curable materials is known. Examples of radiation-curable monomers and oligomers are acrylates and methacrylates of diols, triols and tetrols, polyimides made from aromatic tetracarboxylic acids and aromatic diamines having $C_1$–$C_4$ alkyl groups in at least two ortho-positions to the amino groups, and oligomers containing dialkyl groups, for example dimethylmaleimidyl groups.

The novel storage media may also have additional layers, for example interference or barrier layers. It is also possible to construct storage media having a plurality of (for example two) storage layers. The construction and uses of such materials are known to the person skilled in the art. If interference layers are used, preference is given to those which are arranged between the storage layer and the reflective layer and/or between the storage layer and the substrate and consist of a dielectric material, for example $SiO_2$ or, as described in EP 353 393, of $TiO_2$, $Si_3N_4$, ZnS or silicone resins.

The novel storage media can be produced by processes known per se, it being possible to use various coating methods depending on the materials used and their function.

Suitable coating methods are, for example, dipping, pouring, brushing, knife coating and spin coating, and vapour-deposition processes carried out in a high vacuum. Pouring processes, for example, are generally carried out using solutions in organic solvents. If solvents are used, it must be ensured that the supports used are insensitive to these solvents. Suitable coating methods and solvents are described, for example, in EP 401 791.

If the storage layer is applied by spin-coating of a solution of the compound of the formula (I) or (II), the solvents used are preferably alcohols, for example 2-methoxyethanol, isopropanol, isobutanol or n-butanol, or fluorinated alcohols, for example 2,2,2-trifluoroethanol or 2,2,3,3-tetrafluoro-1-propanol, or mixtures thereof.

However, owing to the low solubility of most of the compounds of the formula (I) or (II), the storage layer is preferably applied by vapour-deposition of the compound of the formula (I) or (II). Suitable methods for this purpose are known per se, for example from U.S. Pat. No. 4,578,334 or J. Vac. Sci. Technol. A6(3), 1907–1911 (1988). Vapour deposition usually gives a layer containing the compound of the formula (I) or (II) in the form which has the lower $k_{650}$ value. In general, this is a substantially amorphous, red form, which is known for some of the compounds according to the invention and can be converted into a crystalline form having a higher $k_{650}$ value as described above.

The metallic reflection layer is preferably applied by sputtering, vacuum vapour deposition or chemical vapour deposition (CVD). The sputtering method is particularly preferred owing to the high adhesive strength to the support for the application of the metallic reflection layer. These methods are known and are described in textbooks (for example J. L. Vossen and W. Kern, "Thin Film Processes", Academic Press, 1978).

The construction of the novel storage medium depends principally on the reading method; known function principles are measurement of the change in transmission or, preferably, in reflection.

If the storage material is constructed in accordance with the change in reflection, the following structures, for example, can be used: transparent support/storage layer (if desired multilayer)/reflection layer and, if advantageous, protective layer (not necessarily transparent), or support (not necessarily transparent)/reflection layer/storage layer and, if advantageous, transparent protective layer. In the former case, the light is incident from the support side, while in the latter case the radiation is incident from the storage layer side or, if present, from the protective layer side. In both cases, the light detector is on the same side as the light source. The former construction of the storage material to be used in accordance with the invention is generally preferred.

If the storage material is constructed in accordance with the change in light transmission, the following other structure, for example, is suitable: transparent support/storage layer (if desired multilayer) and, if advantageous, transparent protective layer. The writing and reading light can be incident either on the support side or on the storage layer side or, if present, the protective layer side, the light detector in this case always being on the opposite side.

In addition, further suitable structures are those in which, for example, the storage material is constructed in accordance with the change both in reflection and in transmission, in which case the reflector is replaced by a semitransparent layer, through which, for example, a further storage layer can be addressed.

The writing and reading of the data are carried out by means of laser radiation focused on the storage layer. The writing is carried out at a wavelength in the range from 400 to 700 nm, preferably from 600 to 700 nm, particularly preferably from 630 to 670 nm, for example at 650 nm, and can be achieved pit by pit with a continuous or modulated laser beam. Modulation may be generated directly or, if desired, with the aid of a light modulator. In particular, marks (pits) of precise, but different length can be written, for example having a length of from 0.614 to 2.863 $\mu$m in steps of 0.205 $\mu$m or preferably from 0.4 to 1.87 $\mu$m in steps of 0.133 $\mu$m. The reading is preferably carried out at a wavelength in the range from 600 to 700 nm, particularly preferably from 630 to 670 nm, for example at 650 nm. The laser power is reduced during reading compared with writing, for example by from 10 to 100-fold, in order to prevent the stored data from being changed.

The writing and reading are particularly preferably carried out at the same wavelength, for example at 650 nm. Examples of suitable lasers are commercially available gas lasers, such as He—Cd and He—Ne lasers and argon and krypton ion lasers, frequency-doubled solid-state lasers, such as Nd:YAG lasers, and/or in particular semiconductor diode lasers, such as InGaAlP, ZnSSe/ZnCdSe or GaN diode lasers. Preference is given to InGaAlP diode lasers.

The conditions for writing data on the novel storage medium depend principally on the morphology of the storage layer, which can be prepared either in the predominantly amorphous phase or in the predominantly crystalline phase, and the writing speed, which is preferably between 1 and 10 m/s, particularly preferably between 3 and 6 m/s, for example 4 m/s.

Marks having the higher $k_{650}$ value are preferably written with essentially continuous laser radiation, particularly preferably at a radiation energy density of from 0.2 to 20 kJ/m$^2$ (nJ/$\mu$m$^2$), for example 2 kJ/m$^2$, corresponding to a radiation intensity of 10 GW/m$^2$ (mW/$\mu$m$^2$) at a writing speed of 4 m/s.

Laser radiation is essentially continuous if its power is not interrupted during writing of an individual mark.

Marks having the lower $k_{650}$ value are written using modulated or continuous laser radiation, preferably modulated radiation with a modulation frequency of from 1 to 50 MHz, a mark-to-space ratio preferably of from 1:1 to 5:1 and a mean radiation energy density of from 1 to 50 kJ/m$^2$, most preferably from 2 to 20 kJ/m$^2$. The latter can be, for example, 4 kJ/m$^2$, corresponding to a mean radiation intensity of 20 GW/m$^2$ at a writing speed of 4 m/s.

The time between laser ON and laser OFF depends in both cases on the writing speed and on the respective length of the marks to be written; it is, for example, from about 100 to 500 ns at 4 m/s, the time preferably being reduced compared with the mark length taking into account the focus size.

It is preferred to use a higher energy for writing marks having the lower $k_{650}$ value, and a lower energy for writing marks having the higher $k_{650}$ value. Typically, the energy for writing marks having the lower $k_{650}$ value is at least 150%, preferably at least 200%, of the energy for writing marks having the higher value. The absolute value, which depends on the compounds of formula (I) or (II) in the storage layer, can easily be determined from case to case by simple routine experiments.

It is advantageous that the storage layer present in the form having the lower $k_{650}$ value remains in the form having the lower $k_{650}$ value when it is treated with the abovementioned higher energy laser radiation. It is likewise advantageous that the storage layer present in the form having the higher $k_{650}$ value remains in the form having the higher $k_{650}$ value when it is treated with the abovementioned lower energy laser radiation. This makes control of the mark length easier.

Surprisingly, however, it is of little importance whether a continuous or modulated laser radiation is used. Whether the form having the lower or higher $k_{650}$ value is obtained, depends mainly on the amount of energy applied. Hence, it is possible to use simplified recorders, such as having only the capability of continuous or modulated laser radiation.

The invention therefore also relates to a device for the optical writing or modifying of data in the form of marks of different reflectivity by successive targeting of a monochromatic light beam onto various sites (pits) of an instant optical storage medium, characterized in that the marks of different reflectivity are generated using only continuous laser radiation or only modulated laser radiation.

The invention furthermore relates to a process for the optical writing or reading of data by successive targeting of a monochromatic light beam onto various sites (pits) of a storage layer which can be modified thereby, wherein the storage layer comprises a compound of the formula (I) or (II). The writing or reading is preferably carried out in the wavelength range from 400 to 700 nm, particularly preferably from 630 to 670 nm.

Surprisingly, the novel optical storage media have better resolution than known optical storage media, so that shorter marks and a higher storage density can be achieved. Particular preference is given to a process for optical writing, storage or reading of data using a novel storage medium, where the writing or reading is carried out at a wavelength of from 400 to 700 nm, wherein the smallest length difference between marks of different storage value is less than 0.25 $\mu$m. The smallest length difference between marks of different storage value is particularly preferably less than 0.18 $\mu$m.

Also of very particular importance is the extremely surprising property of the compounds of the formula (I) or (II) according to the invention, that the marks of a storage layer previously written to by means of lower energy laser radiation can be erased again by overwriting by means of higher energy laser radiation, and that, conversely, the marks of a storage layer previously written to by means of higher energy laser radiation can likewise be erased by overwriting by means of lower energy laser radiation. The form having the lower $k_{650}$ value can thus be converted into the form having the higher $k_{650}$ value, and vice versa.

Thus, the marks written under the abovementioned conditions can be modified (overwritten, corrected or erased) selectively at the same relative movement speed of the laser compared with the storage medium as during writing. This enables to combine writing and erasing pits in a single pass. Of course, it is also possible first to erase a whole track, and then to write pits on it, or conversely. The marking and erasing cycle can be repeated as often as desired.

The invention accordingly also relates to a process for modifying data written or stored in the form of marks of different reflectivity by successive targeting of a monochromatic light beam onto various sites of a storage layer which can be modified thereby, wherein the storage layer comprises a compound of the formula (I) or (II).

In the novel overwriting or erasing process, the written or stored data is preferably modified optically by overwriting amorphous marks in a crystalline storage layer using modulated laser radiation and crystalline marks in an amorphous storage layer using essentially continuous laser radiation.

The modification or erasing is particularly preferably carried out using a laser having the same wavelength as during writing.

The novel overwriting or erasing process can also be used for writing onto a storage medium in which the compound of the formula (I) or (II) is in the form having the lower $k_{650}$ value. For example, writing can take place onto the freshly vapour-deposited form.

The novel process enables storage of data with high reliability and durability, very good mechanical and thermal stability and high light stability and sharp edge zones. The surprisingly high signal/noise ratio of support material to data marking is particularly advantageous, allowing error-free reading. The high storage capacity is particularly valuable in the video sector.

The invention therefore also relates to a novel storage medium on which optically readable marks of different reflectivity are stored.

The data are read by methods known per se by recording the change in absorption or reflection using laser radiation, for example as described in "CD-Player und R-DAT Recorder" (Claus Biaesch-Wiepke, Vogel Buchverlag, Würzburg, 1992). This is preferably carried out using a laser having the same wavelength as during writing and erasing.

The novel data-carrying medium is, in particular, an optical data material of the writable, preferably writable and erasable or overwritable type. It can be used, for example, as a playable DVD-R or DVD-RAM storage disk, as a storage material for computers, as an identity or security card, for laser inscription by the scanning method or for the production of diffractive optical elements, for example holograms.

The examples below illustrate the invention in greater detail:

EXAMPLE 1

10 g of perylene-3,4,9,10-tetracarboxylic dianhydride, 3.6 g of n-propylamine and 30 ml of water are heated at 130° C. for 10 hours in an autoclave, during which a pressure of 2 bar is established. The mixture is then cooled, and the red suspension is filtered and washed with water until neutral. The filter cake is refluxed for 15 minutes in 100 ml of DMF, filtered while hot and washed with ethanol (EtOH). The residue is dried at 60° C./160 mbar, giving 9.8 g of a dark red powder having the formula:

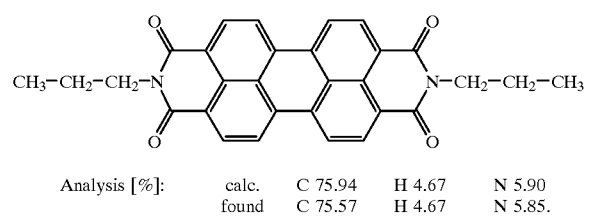

| Analysis [%]: | calc. | C 75.94 | H 4.67 | N 5.90 |
| | found | C 75.57 | H 4.67 | N 5.85. |

EXAMPLE 2

10 g of perylene-3,4,9,10-tetracarboxylic dianhydride, 5.3 g of methoxypropylamine and 30 ml of water are heated at 130° C. for 10 hours in an autoclave, during which a pressure of 2 bar is established. The mixture is then cooled, and the red suspension is filtered and washed with water until neutral. The filter cake is refluxed for 15 minutes in 100 ml of DMF, filtered while hot and washed with EtOH. The residue is dried at 60° C./160 mbar, giving 12.7 g of a red powder having the formula:

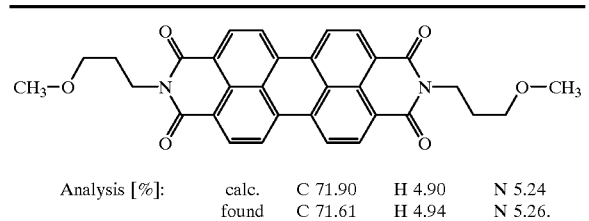

| Analysis [%]: | calc. | C 71.90 | H 4.90 | N 5.24 |
| | found | C 71.61 | H 4.94 | N 5.26. |

EXAMPLE 3

5 g (12.75 mmol) of perylene-3,4,9,10-tetracarboxylic dianhydride, 9.41 g (50.58 mmol) of 4-bromobenzylamine, 5.96 g (50.95 mmol) of n-butylethanolamine and 35 ml of o-dichlorobenzene are introduced into a 250 ml multineck flask fitted with reflux condenser, stirrer and nitrogen inlet, and the mixture is stirred at 160° C. for 24 h, cooled to room temperature, diluted with 100 ml of methanol and filtered. The residue is stirred at 80° C. for 20 minutes in 200 ml of 15% KOH solution, filtered while hot and washed with water until neutral. The residue is dried at 60° C./1125 mbar, giving 8.43 g of a black powder of the formula:

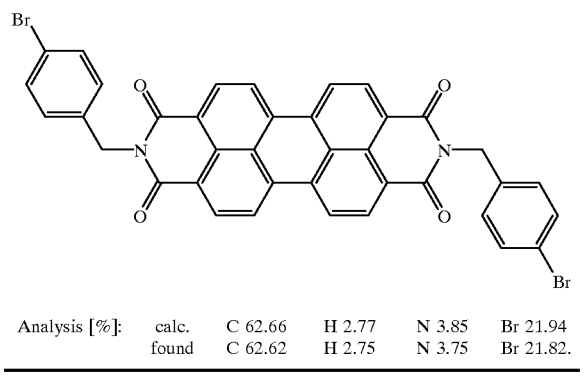

| Analysis [%]: | calc. | C 62.66 | H 2.77 | N 3.85 | Br 21.94 |
| | found | C 62.62 | H 2.75 | N 3.75 | Br 21.82. |

EXAMPLE 4

10 g of perylene-3,4,9,10-tetracarboxylic dianhydride, 8.8 g of 4-(2-aminoethyl)-pyridin and 30 ml of water are heated at 130° C. for 5 hours in an autoclave, during which a pressure of 2 bar is established. The mixture is then cooled, and the red suspension is filtered and washed with water until neutral. The filter cake is refluxed for 10 minutes in 100 ml of DMF, filtered while hot and washed with EtOH. The residue is dried at 60° C./1160 mbar, giving 14.0 g of a red powder having the formula:

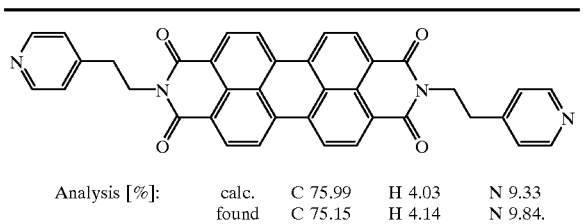

| Analysis [%]: | calc. | C 75.99 | H 4.03 | N 9.33 |
| | found | C 75.15 | H 4.14 | N 9.84. |

EXAMPLE 5

5 g (8.32 mmol) of the compound from Example 4, 11.8 g (83.24 mmol) of methyliodide and 25 ml of DMF are refluxed for 22 hours in a 50 ml multineck flask fitted with reflux condenser, thermometer, stirrer and nitrogen inlet. The mixture is then cooled, diluted with 100 ml of MeOH, stirred for 30 minutes and filtered. The residue is taken up in 80 ml of acetone, refluxed for 30 minutes, then cooled and filtered, and this washing process is repeated twice. The residue is then suspended in 100 ml of petroleum ether, refluxed for 1 hour, filtered while hot and dried at 60° C./160 mbar, giving 6.4 g of a black powder of the formula:

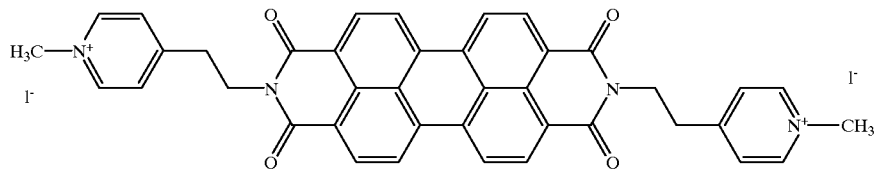

| Analysis [%]: | calc. | C 54.32 | H 3.42 | N 6.33 | I 28.69 |
|---|---|---|---|---|---|
| | found | C 54.14 | H 3.50 | N 6.51 | I 27.77. |

EXAMPLE 6

1.7 g (3.74 mmol) of perylene-1,12-sulfonyl-3,4,9,10-tetracarboxylic dianhydride (prepared as described in U.S. Pat. No. 4,937,164), 1.09 g of 2-phenylethylamine and 5 ml of water are heated at 130° C. for 5 hours in an autoclave, during which a pressure of 2 bar is established. The mixture is then cooled, and the red suspension is filtered and washed with water until neutral. The filter cake is refluxed for 15 minutes in 30 ml of DMF, filtered while hot and washed with EtOH. The residue is dried at 60° C./160 mbar, giving 1.8 g of a dark violet powder having the formula:

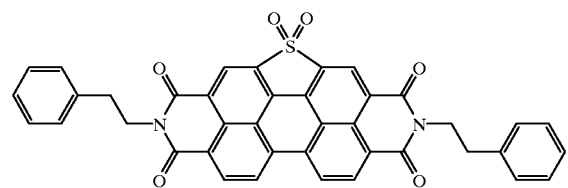

| Analysis [%]: | calc. | C 72.72 | H 3.66 | N 4.24 | S 4.85 |
|---|---|---|---|---|---|
| | found | C 72.63 | H 4.15 | N 4.72 | S 4.47. |

EXAMPLE 7

The procedure is analogous to that of Example 3, but 4-bromobenzylamine is replaced by an equimolar amount of 4-methoxybenzylamine, giving Colour Index Pigment Black 32 of the formula:

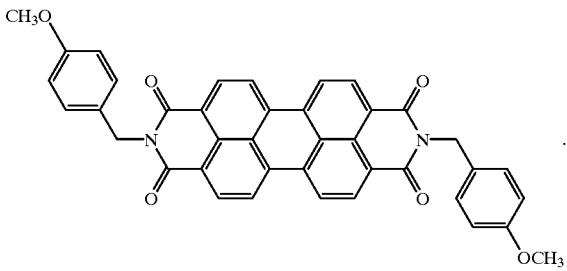

EXAMPLE 8

2 g (3.33 mmol) of the compound from Example 4, 6.2 g (33.3 mmol) of methyl p-toluenesulfonate and 12 ml of DMF are refluxed for 16 hours in a 50 ml multineck flask fitted with reflux condenser, thermometer, stirrer and nitrogen inlet. The mixture is then cooled, diluted with 50 ml of methanol, stirred for 30 minutes and filtered. The residue is taken up in 80 ml of acetone, refluxed for 15 minutes, then cooled and filtered, and this washing process is repeated twice. The residue is then suspended in 100 ml of petroleum ether, refluxed for 1 hour, filtered while hot and dried at 50° C./160 mbar, giving 2 g of a dark red powder of the formula:

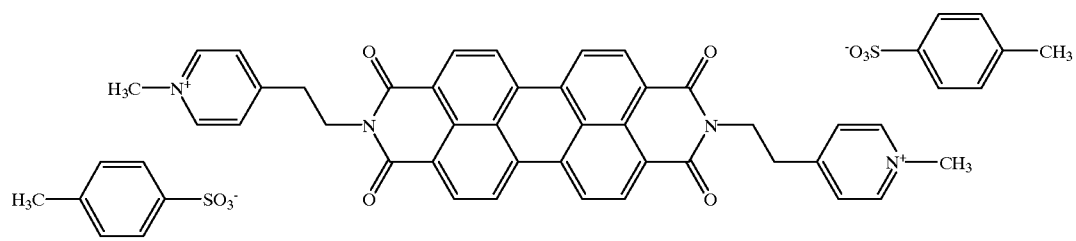

| Analysis [%]: | calc. | C 66.65 | H 4.55 | N 5.75 | S 6.59 |
|---|---|---|---|---|---|
| | found | C 63.69 | H 4.49 | N 4.85 | S 5.44. |

EXAMPLE 9

10 g (25.5 mmol) of perylene-3,4,9,10-tetracarboxylic dianhydride, 5.2 g (60 mmol) of n-pentylamine and 50 g of imidazol are heated at 160° C. for 1 hour in an autoclave. The reaction mixture is then cooled, 200 ml of DMF are added, the mixture is refluxed for 15 minutes and filtered while hot, and the residue is washed with DMF and dried at 60° C./160 mbar, giving 12 g of a red powder of the formula:

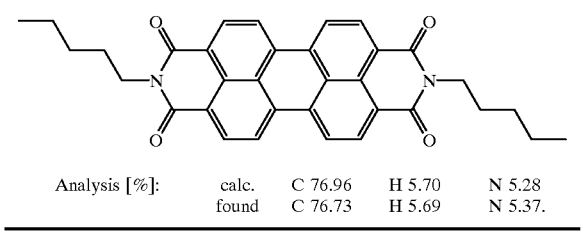

Analysis [%]:   calc.    C 76.96   H 5.70   N 5.28
                found    C 76.73   H 5.69   N 5.37.

EXAMPLE 10

The procedure is analogous to Example 9, but the n-pentylamine is replaced by n-butylamine, giving the black product of the formula:

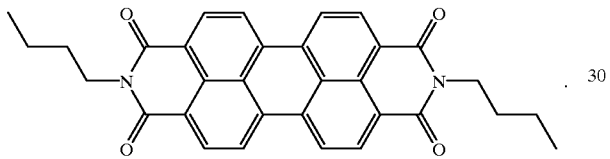

EXAMPLE 11

The procedure is analogous to that of Example 4, but 4-(2-aminoethyl)pyridin is replaced by an equimolar amount of 4-(2-aminoethyl)benzene, giving Colour Index Pigment Black 31 of the formula:

[71132]

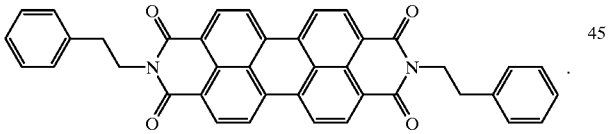

EXAMPLE 12

10 g (25.5 mmol) of perylene-3,4,9,10-tetracarboxylic dianhydride, 5.4 g (71.85 mmol) of 3-amino-1-propanol and 30 ml of water are heated at 130° C. for 7 hours in an autoclave, during which a pressure of 2 bar is established. The mixture is subsequently cooled, and the brown suspension is filtered, washed with 80 ml of 1 % aqueous $Na_2CO_3$ solution until the filtrate is colourless and then washed with water until neutral. The filter cake is suspended in 100 ml of DMF, refluxed for 10 minutes, filtered while hot and dried at 50° C./160 mbar, giving 12 g of a brown-red powder of the formula:

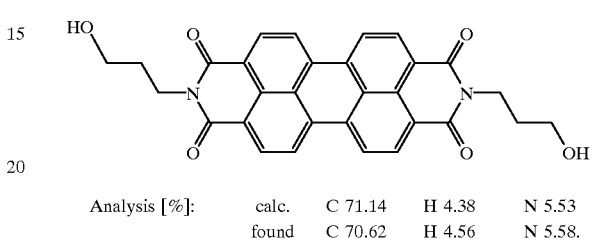

Analysis [%]:   calc.    C 71.14   H 4.38   N 5.53
                found    C 70.62   H 4.56   N 5.58.

EXAMPLE 13

The procedure is analogous to Example 12, but the 3-amino-1-propanol is replaced by 4-amino-1-butanol, giving the product of the formula:

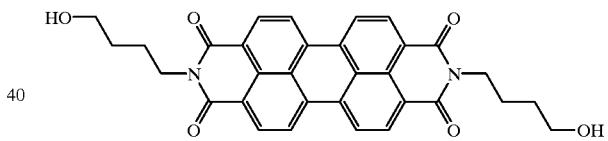

EXAMPLE 14

The procedure is analogous to that of Example 12, but the 3-amino-1-propanol is replaced by 6-amino-1-hexanol, giving the product of the formula:

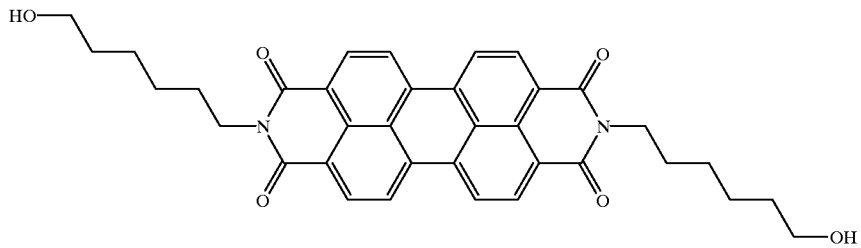

EXAMPLE 15

11.9 g (98.12 mmol) of phenylethylamine and 150 ml of water are introduced into a 500 ml multinecked flask fitted with reflux condenser, thermometer, nitrogen inlet and stirrer, and the mixture is cooled to 0–5° C. 10 g (22.3 mmol) of perylene-3,4,9,10-tetracarboxylic monoanhydride monopotassium salt (prepared as described by H. Tröst, Dyes and Pigments 4,171 (1983)) are then added, and the reaction mixture is stirred for 4 hours at room temperature and for a further 2 hours at 90° C. 33.4 g of 20% HCl solution are then added, and the dark-red suspension is stirred for 2 hours at 90° C. The cooled reaction mixture is filtered, and the filter cake is washed with 200 ml of water. The brown-red solid is taken up in 180 ml of 10% KOH solution and stirred for 2 hours at 90° C. The mixture is then cooled and filtered, and the filter cake is washed with 100 ml of 8% KCl solution and 100 ml of 2% $K_2CO_3$ solution until the filtrate appears colourless. The residue is dissolved in 600 ml of hot water and filtered while hot, and the filtrate is adjusted to pH 3 at 90° C. using 5 ml of 37% HCl solution. The mixture is cooled to 20° C., and the brown-red precipitate is filtered off, washed with water and dried at 50° C./160 mbar, giving 12.1 g of a brown-red powder of the following formula:

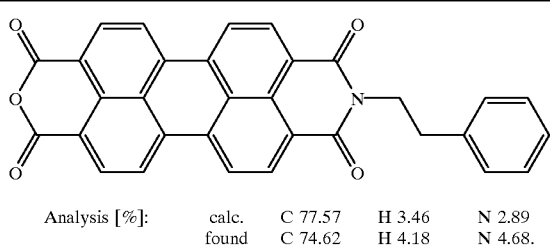

| Analysis [%]: | calc. | C 77.57 | H 3.46 | N 2.89 |
|---|---|---|---|---|
| | found | C 74.62 | H 4.18 | N 4.68. |

EXAMPLE 16

5 g (10.13 mmol) of the compound from Example 15, 4 g (36.22 mmol) of 50% KOH, 2.9 g (22.64 mmol) of hydrazine sulfate, 67 ml of Methylcellosolve and 33 ml of water are heated for 3 hours at 135° C. in an autoclave, during which a pressure of 2 bar is established. The mixture is then diluted with water and filtered, and the filter cake is washed with water. The black solid is taken up in 100 ml of DMF, refluxed for 15 minutes, filtered while hot and washed with EtOH. The residue is dried at 60° C./160 mbar, giving 4.6 g of a brown-black powder of the formula:

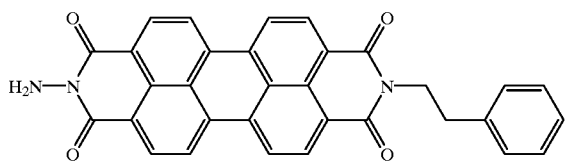

| Analysis [%]: | calc. | C 75.43 | H 3.76 | N 8.25 |
|---|---|---|---|---|
| | found | C 74.26 | H 4.05 | N 6.04. |

EXAMPLE 17
The brown-green compound of the formula:

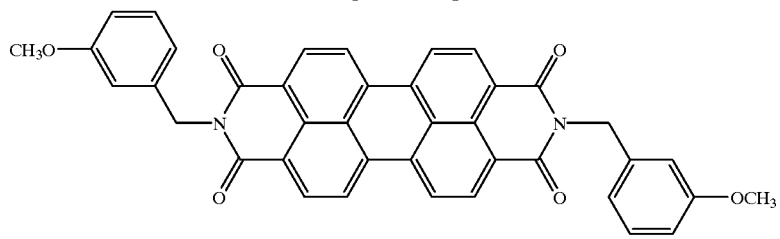

is obtained analogously to the preceding examples.

| Analysis [%]: | calc. | C 76.18 | H 4.16 | N 4.44 |
|---|---|---|---|---|
| | found | C 75.80 | H 4.23 | N 4.54. |

EXAMPLE 18

The red compound of the formula:

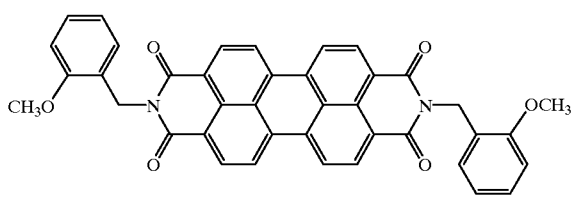

is obtained analogously to the preceding examples.

| Analysis [%]: | calc. | C 76.18 | H 4.16 | N 4.44 |
|---|---|---|---|---|
| | found | C 75.45 | H 4.25 | N 4.68. |

EXAMPLE 19

The red compound of the formula:

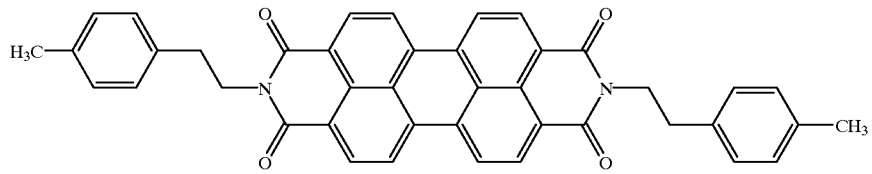

is obtained analogously to the preceding examples.

| Analysis [%]: | calc. | C 80.49 | H 4.82 | N 4.47 |
|---|---|---|---|---|
| | found | C 80.04 | H 4.93 | N 4.34. |

EXAMPLE 20

The red-brown compound of the formula:

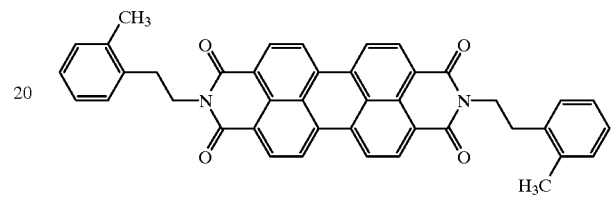

is obtained analogously to the preceding examples.

| Analysis [%]: | calc. | C 80.49 | H 4.82 | N 4.47 |
|---|---|---|---|---|
| | found | C 78.76 | H 4.72 | N 4.52. |

EXAMPLE 21

The red-violet compound of the formula:

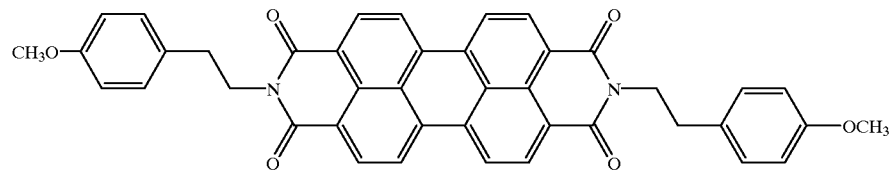

is obtained analogously to the preceding examples.

| Analysis [%]: | calc. | C 76.58 | H 4.59 | N 4.25 |
|---|---|---|---|---|
| | found | C 75.85 | H 4.62 | N 4.28. |

EXAMPLE 22

The red-brown compound of the formula:

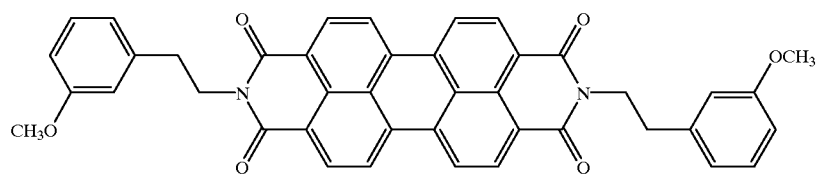

is obtained analogously to the preceding examples.

| Analysis [%]: | calc. | C 76.58 | H 4.59 | N 4.25 |
|---|---|---|---|---|
| | found | C 75.78 | H 4.61 | N 4.20. |

EXAMPLE 23

The orange-red compound of the formula:

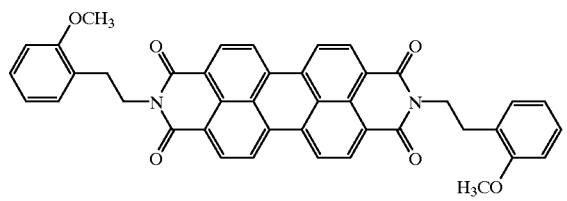

is obtained analogously to the preceding examples.

| Analysis [%]: | calc. | C 76.58 | H 4.59 | N 4.25 |
|---|---|---|---|---|
| | found | C 75.89 | H 4.62 | N 4.18. |

EXAMPLE 24

The black-red compound of the formula:

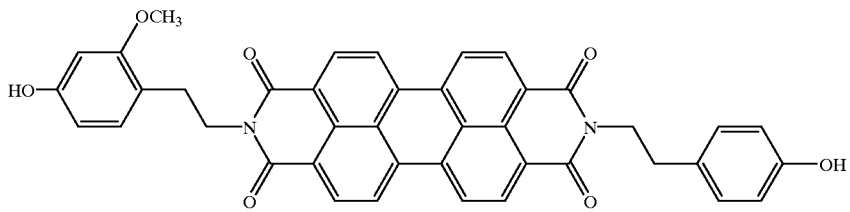

is obtained analogously to the preceding examples.

| Analysis [%]: | calc. | C 76.18 | H 4.16 | N 4.44 |
|---|---|---|---|---|
| | found | C 74.29 | H 4.34 | N 4.45. |

EXAMPLE 25

The red compound of the formula:

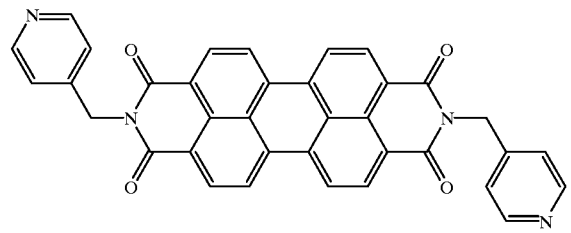

is obtained analogously to the preceding examples.

| Analysis [%]: | calc. | C 75.52 | H 3.52 | N 9.79 |
|---|---|---|---|---|
| | found | C 73.73 | H 3.78 | N 9.61. |

EXAMPLE 26

The red compound of the formula:

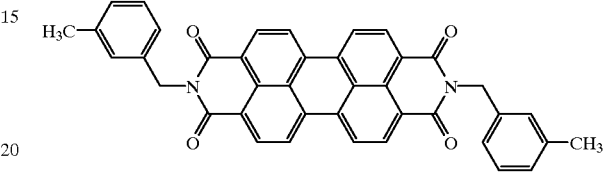

is obtained analogously to the preceding examples.

| Analysis [%]: | calc. | C 79.98 | H 4.70 | N 4.66 |
|---|---|---|---|---|
| | found | C 79.74 | H 4.68 | N 4.89. |

EXAMPLE 27

The red compound of the formula:

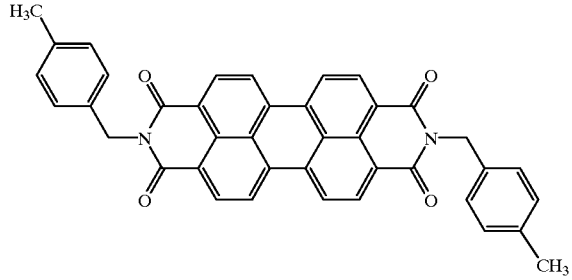

is obtained analogously to the preceding examples.

| Analysis [%]: | calc. | C 80.25 | H 4.38 | N 4.68 |
|---|---|---|---|---|
| | found | C 79.34 | H 4.53 | N 4.87. |

EXAMPLE 28

The red-brown compound of the formula:

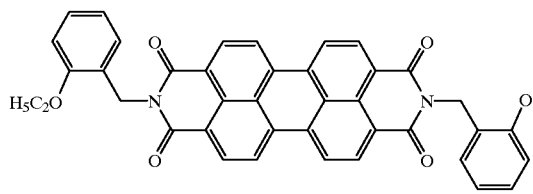

is obtained analogously to the preceding examples.

| Analysis [%]: | calc. | C 76.58 | H 4.59 | N 4.25 |
|---|---|---|---|---|
| | found | C 76.60 | H 4.63 | N 4.29. |

EXAMPLE 29

The dark red compound of the formula:

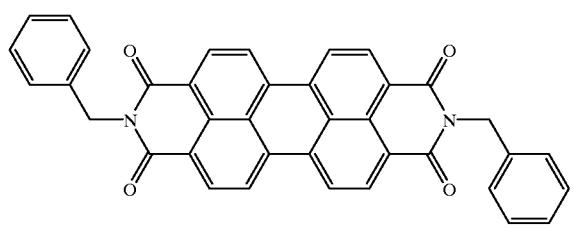

is obtained analogously to the preceding examples.

| Analysis [%]: | calc. | C 79.99 | H 3.89 | N 4.91 |
|---|---|---|---|---|
| | found | C 79.57 | H 4.10 | N 4.99. |

EXAMPLE 30

The red compound of the formula:

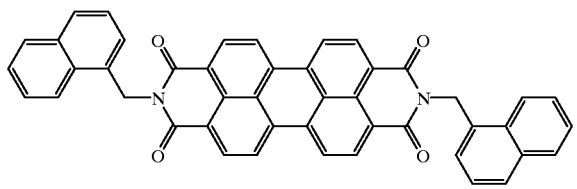

is obtained analogously to the preceding examples.

| Analysis [%]: | calc. | C 82.37 | H 3.91 | N 4.18 |
|---|---|---|---|---|
| | found | C 81.40 | H 3.96 | N 3.78. |

EXAMPLE 31

The brown compound of the formula:

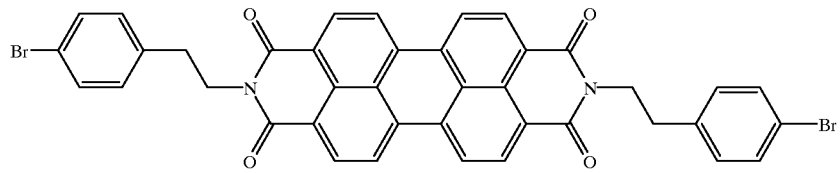

is obtained analogously to the preceding examples.

| Analysis [%]: | calc. | C 63.51 | H 3.20 | N 3.70 | Br 21.13 |
|---|---|---|---|---|---|
| | found | C 63.53 | H 3.30 | N 3.51 | Br 20.93. |

EXAMPLE 32

The red compound of the formula:

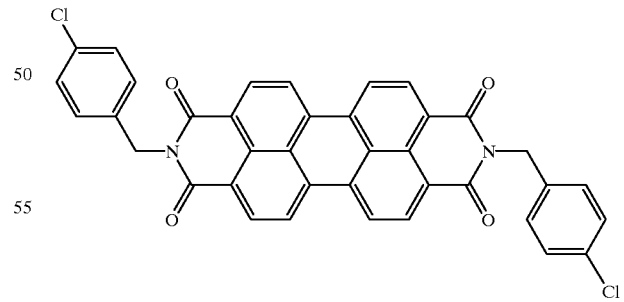

is obtained analogously to the preceding examples.

| Analysis [%]: | calc. | C 71.37 | H 3.15 | N 4.38 | Cl 11.09 |
|---|---|---|---|---|---|
| | found | C 70.46 | H 3.05 | N 4.43 | Cl 11.05. |

EXAMPLE 33

The brown-red compound of the formula:

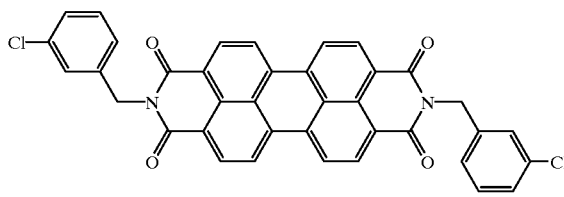

is obtained analogously to the preceding examples.

| Analysis [%]: | calc. | C 71.37 | H 3.15 | N 4.38 | Cl 11.09 |
|---|---|---|---|---|---|
| | found | C 70.97 | H 3.09 | N 4.49 | Cl 11.02. |

EXAMPLE 34

The red compound of the formula:

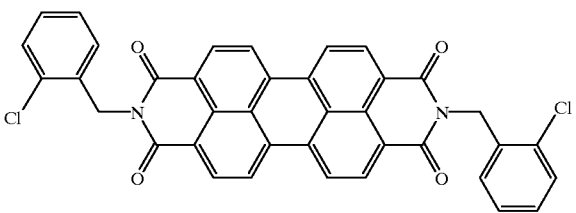

is obtained analogously to the preceding examples.

| Analysis [%]: | calc. | C 71.37 | H 3.15 | N 4.38 | Cl 11.09 |
|---|---|---|---|---|---|
| | found | C 68.65 | H 3.10 | N 4.26 | Cl 10.73. |

EXAMPLE 35

The orange-red compound of the formula:

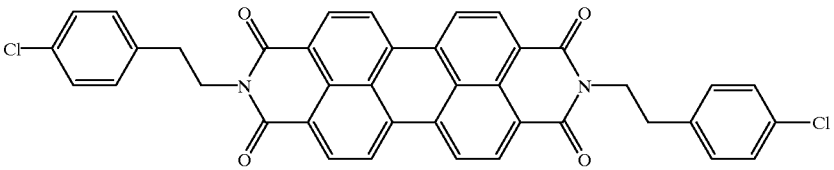

is obtained analogously to the preceding examples.

| Analysis [%]: | calc. | C 71.97 | H 3.62 | N 4.20 | Cl 10.62 |
|---|---|---|---|---|---|
| | found | C 71.86 | H 3.49 | N 4.32 | Cl 10.90. |

EXAMPLE 36

The black compound of the formula:

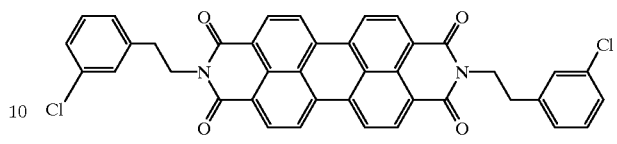

is obtained analogously to the preceding examples.

| Analysis [%]: | calc. | C 71.97 | H 3.62 | N 4.20 | Cl 10.62 |
|---|---|---|---|---|---|
| | found | C 71.71 | H 3.48 | N 4.03 | Cl 10.61. |

EXAMPLE 37

The red-brown compound of the formula:

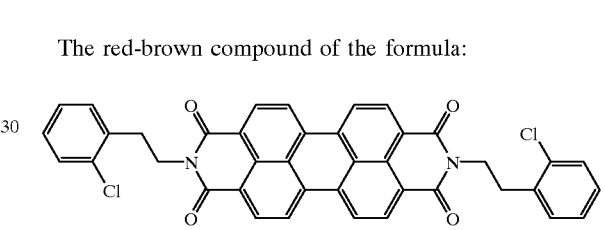

is obtained analogously to the preceding examples.

| Analysis [%]: | calc. | C 71.97 | H 3.62 | N 4.20 | Cl 10.62 |
|---|---|---|---|---|---|
| | found | C 71.67 | H 3.40 | N 4.01 | Cl 10.61. |

EXAMPLE 38

The red compound of the formula:

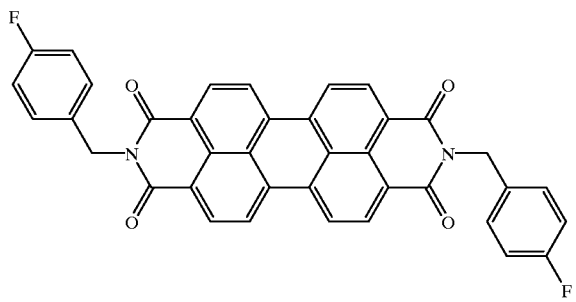

is obtained analogously to the preceding examples.

| Analysis [%]: | calc. | C 75.24 | H 3.32 | N 4.62 | F 6.26 |
| --- | --- | --- | --- | --- | --- |
| | found | C 74.46 | H 3.49 | N 4.83 | F 6.03. |

EXAMPLE 39

The red-brown compound of the formula:

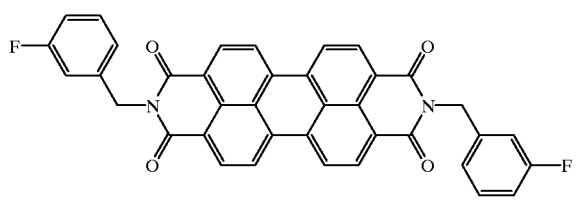

is obtained analogously to the preceding examples.

| Analysis [%]: | calc. | C 75.24 | H 3.32 | N 4.62 | F 6.26 |
| --- | --- | --- | --- | --- | --- |
| | found | C 75.04 | H 3.43 | N 4.64 | F 5.96. |

EXAMPLE 40

The red compound of the formula:

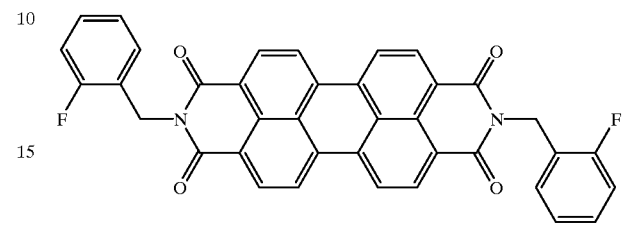

is obtained analogously to the preceding examples.

| Analysis [%]: | calc. | C 75.24 | H 3.32 | N 4.62 | F 6.26 |
| --- | --- | --- | --- | --- | --- |
| | found | C 74.56 | H 3.40 | N 4.72 | F 6.00. |

EXAMPLE 41

The dark red compound of the formula:

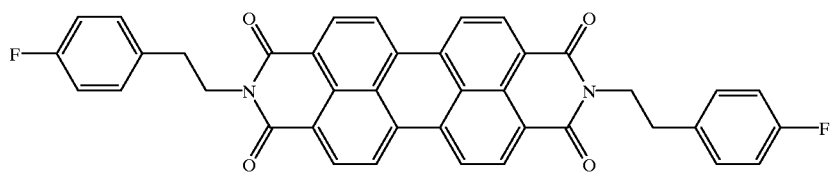

is obtained analogously to the preceding examples.

| Analysis [%]: | calc. | C 75.70 | H 3.81 | N 4.41 | F 5.99 |
| --- | --- | --- | --- | --- | --- |
| | found | C 75.34 | H 3.88 | N 4.29 | F 6.02. |

EXAMPLE 42

The rust red compound of the formula:

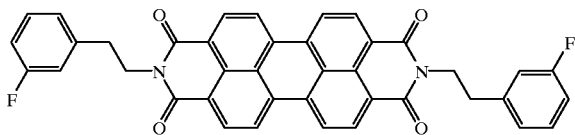

is obtained analogously to the preceding examples.

| Analysis [%]: | calc. | C 75.70 | H 3.81 | N 4.41 | F 5.99 |
| --- | --- | --- | --- | --- | --- |
| | found | C 74.96 | H 3.70 | N 4.12 | F 5.90. |

EXAMPLE 43

The red-brown compound of the formula:

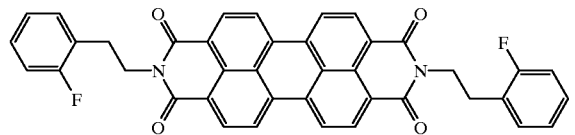

is obtained analogously to the preceding examples.

| Analysis [%]: | calc. | C 75.70 | H 3.81 | N 4.41 | F 5.99 |
| --- | --- | --- | --- | --- | --- |
| | found | C 75.38 | H 3.85 | N 4.30 | F 6.00. |

EXAMPLE 44

5 g (8.73 mmol) of the compound of Example 25 and 12.4 g (87.30 mmol) of methyl iodide are reacted analogously to Example 5 to give 6.2 g of the compound of the following formula in the form of a brown-red powder:

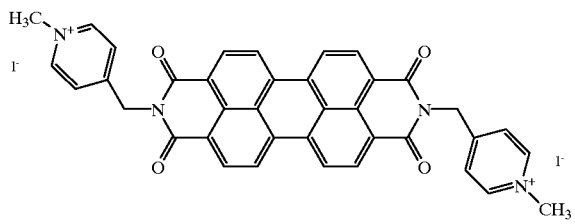

| Analysis [%]: | calc. | C 53.17 | H 3.29 | N 6.53 |
| --- | --- | --- | --- | --- |
| | found | C 53.74 | H 3.25 | N 6.57. |

EXAMPLE 45

80 nm of Colour Index Pigment Black 31 is vapour-deposited onto a polycarbonate support (thickness 0.6 mm/diameter 120 mm) at a coating rate of 0.6 nm/s in a vacuum vapour deposition apparatus (Balzers) in a high vacuum (1.3 mPa) from a resistance-heated crucible. A 70 nm reflection layer of aluminium is then applied. A UV-crosslinkable photopolymer (TMSD-1 7, Dainippon Ink) is then applied in a thickness of 7 μm by spin coating and crosslinked by means of UV light. At 650 nm, the storage layer has a reflectivity of 63%. Using a 25 mW HeNe-laser having a wavelength of 633 nm and a focusing optical system having a numerical aperture of 0.5, marks having a width of 1 μm are written into the storage layer at a power of 8 mW and a speed of rotation of 0.5 m/s. A change in reflection from 63% to 30% is measured at the written points by means of a microscope spectrophotometer. The marks are then overwritten by means of a pulsed dye laser (15 ns pulse length) at 635 nm with an energy density of 2 kJ/m$^2$. The reflectivity changes from 30% to 55%. The operation can be repeated a number of times.

EXAMPLE 46

An optical recording medium is made in a similar manner to Example 45 using the compound of Example 7. At 635 nm, the storage layer has a reflectivity of 68%. Using a 25 mW HeNe-laser having a wavelength of 633 nm and a focusing optical system having a numerical aperture 0.5, marks having a width of 1 μm are written into the storage layer at a power of 20 mW and a speed of rotation of 0.1 m/s. A change in reflection from 68% to 45% is measured at the written points by means of a microscope spectrophotometer. The marks are then overwritten by means of a pulsed dye laser (15 ns pulse length) at 635 nm with an energy density of 2 kJ/m$^2$. The reflectivity changes from 45% to 75%. The operation can be repeated a number of times.

EXAMPLE 47

An optical recording medium is made in a similar manner to Example 45 but using the compound of Example 1. At 635 nm, the storage layer has a reflectivity of 38%.

Using a 25 mW HeNe-laser having a wavelength of 633 nm and a focusing optical system having a numerical aperture 0.5, marks having a width of 1 μm are written into the storage layer at a power of 20 mW and a speed of rotation of 2 m/s. A change in reflection from 38% to 20% is measured at the written points by means of a microscope spectrophotometer. The marks are then overwritten by means of a pulsed dye laser (15 ns pulse length) at 635 nm with an energy density of 2 kJ/m$^2$. The reflectivity changes from 20% to 40%. The operation can be repeated a number of times.

EXAMPLE 48

A red solid layer is vapour-deposited onto a glass support as described in Example 45 and measured by means of a spectral ellipsometer (Sopra). At the writing wavelength of 650 nm, a refractive index of n−ik=2.15−i0.1 is determined. The layer is then transformed thermally into the black phase, and a refractive index of n−ik=2.2−i 0.4 is determined at 650 nm.

EXAMPLES 49–54

The procedure is analogous to that of Example 45, but the Pigment Black 31 is replaced by a compound of Examples 1, 2, 3, 4, 6 and 7, respectively.

EXAMPLE 55

The procedure is analogous to that of Example 45, but the Pigment Black 31 is replaced by the compound of Example 5, which is not vapour-deposited, but instead coated by spin-coating from a tetrafluoropropanol solution.

EXAMPLE 56

A 5S nm thick layer of the compound of Example 6 is coated by vacuum evaporation on a polycarbonate substrate having a thickness of 0.6 mm, a diameter of 120 mm and a spiral groove formed on its surface with a depth of 30 nm, a width of 0.3 µm, and a pitch of 0.8 Wm. On this red recording layer, a 60 nm thick aluminium layer is sputtered to form the reflective layer followed by a protection film (photocurable resin).

The so-obtained optical recording medium is first initialized by 2 erasing cycles with a commercial tester DDU-1000 (available from Pulstec Industrial, Japan) with a red semiconductor laser head of 635 nm at a linear speed of 3.9 m/s with 8.5 mW erasing power. The initial reflectivity drops from 40% to 20%. The disc is than recorded with a laser power of 12 mW, and consequently the reflectance goes up from 20% to 30%. The recording strategy is essentially continuous. The disc can be then overwritten several times.

EXAMPLE 57

The procedure is analogous to that of Example 56, but with a modulated laser radiation. The laser power for erasing is 7 mW. The initial reflectivity drops from 40% to 22%. The recording signal consists of a starting pulse of 76 ns followed by a sequence of short pulses of 33 ns each, the time interval between each pulse is 5 ns. The disc is recorded on the land with a laser power of 12 mW, and consequently the reflectance goes up from 22% to 29%. The disc can be overwritten and erased several times.

EXAMPLE 58

The procedure is analogous to that of Example 57, but recorded in the grooves. After the initial erasing cycles the initial reflectivity drops from 40% to 20%. After recording the reflectance goes up from 20% to 26%. The disc can be overwritten and erased several times.

EXAMPLE 59

A 70 nm thick layer of the compound of Example 1 is coated by vacuum evaporation on a polycarbonate substrate having a thickness of 0.6 mm, a diameter of 120 mm and a spiral groove formed on its surface with a depth of 70 nm, a width of 0.3 µm, and a pitch of 0.8 µm. On this red recording layer, a 60 nm thick gold layer is sputtered to form the reflective layer followed by a protection film (photocurable resin). The optical medium obtained is first initialized by 5 erasing cycles with the DDU-1000 tester as used in Example 56 at a linear speed of 2.5 m/s with 7.5 mW erasing power. The initial reflectivity drops from 25% to 18%. The disc is than recorded with a laser power of 12 mW, and consequently the reflectance goes up from 18% to 28%. The disc can be overwritten and erased several times.

EXAMPLE 60

A 70 nm thick layer of the compound of Example 43 is coated at a rate of 0.1 nm/s by vacuum evaporation on a polycarbonate substrate having a thickness of 0.6 mm, a diameter of 120 mm and a spiral groove formed on its surface with a depth of 30 nm, a width of 0.3 µm, and a pitch of 0.8 µm. On this recording layer, a 60 nm thick gold layer is sputtered to form the reflective layer followed by a protection film.

The so-obtained optical recording medium is recorded with the DDU-1000 tester at a linear speed of 3.9 m/s with 12 mW recording laser power. The initial reflectivity goes up from 20% to 32%. The written marks are then erased with a laser power of 6.5 mW, the reflectance falls down from 32% to 22%. The recording strategy is essentially continuous. The disc can be then overwritten and erased several times. The recording can be performed both in grooves and on land.

EXAMPLE 61

An optical recording medium is made similarly to Example 60, but using the compound of Example 12, evaporated at a rate of 1 nm/s. The medium is recorded at a linear speed of 3.9 m/s with 12 mW recording power. The initial reflectance changes from 42% to 34% after recording. The so obtained medium is read 1000 times using a 0.5 mW laser light having a wavelength of 635 nm without any signal deterioration.

EXAMPLE 62

An optical recording medium is made similarly to Example 60, but using the compound of Example 33 and evaporating a 205 nm thick layer at a rate of 1 nm/s. After recording at a linear speed of 2.5 m/s, the reflectance changes from 32% to 26%.

EXAMPLE 63

A 70 nm thick film of the compound of Example 15 is evaporated on a glass substrate. The film as deposited has an optical density of 0.43 at 500 nm and 0.42 at 420 nm. After heating on a hot plate at 70° C. for 2 minutes. the film has an optical density of 0.33 at 500 nm and 0.22 at 420 nm.

EXAMPLE 64

A 70 nm thick film of the compound of Example 16 is evaporated on a glass substrate and heated on a hot plate at 200° C. for 1 minute. The spectral analysis was done according to the procedure of Example 50. The optical density change at 635 nm is 0.17.

EXAMPLE 65–67

Similarly to the previous Examples, a solid recording film is formed by spin-coating a tetrafluoropropanol solution of the compounds of Examples 5, 8, respectively 44.

EXAMPLE 68

A 70 nm thick film of the compound of Example 43 is evaporated on a glass substrate. The dark brown layer turns red after pressing a stylus with a force of 2.108 g/m$^2$.

What is claimed is:

1. An optical storage medium comprising a substrate and a storage layer, wherein the storage layer comprises a compound of the formula

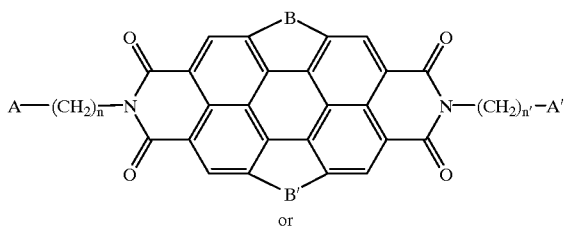

(I)

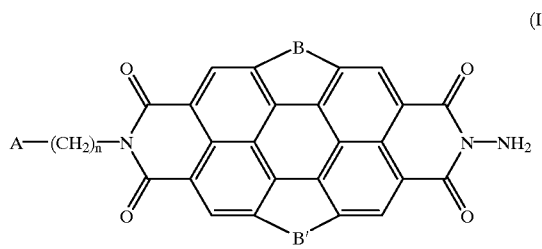

(II)

in which A and A', independently of one another, are unsubstituted or mono- or di-halo-, -hydroxy-, —$C_1$–$C_6$alkyl-, —$C_1$–$C_6$alkoxy-, -cyano- or -nitro- substituted phenyl, pyridyl, pyrrolyl, imidazolyl, furyl or thienyl, which can, if desired, be fused to a benzene ring, are halide, tetrafluoroborate or unsubstituted or with one or more halogen substituted $C_1$–$C_6$alkanesulfonate, benzenesulfonate, $C_1$–$C_6$alkylbenzenesulfonate, $C_1$–$C_6$alkylsulfate or di-$C_1$–$C_6$alkyl-phosphonate of N-$C_1$–$C_6$alkyl-pyridiniumyl, or are unsubstituted or mono- or di-hydroxy-substituted $C_2$–$C_6$alkyl or $C_2$–$C_6$alkenyl, whose chain may be uninterrupted or interrupted by one or two oxygen atoms, B and B', independently of one another, are 2 H, S, $S_2$ or $SO_2$, and n and n', independently of one another, are each a number from 1 to 4, with the proviso that a compound of the formula (I) or (II) is comprised in said storage layer, which is not of the formula

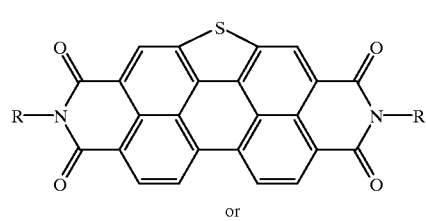

(III)

or

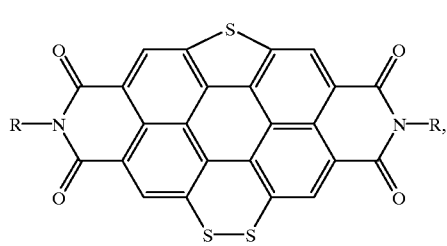

(IV)

wherein R is independently selected from the group consisting of hydrogen, aryl, alkyl, substituted aryl, substituted alkyl, alkoxy, aryl alkyl or aryloxy.

2. An optical storage medium according to claim 1, in which n and n' are each a number 1 or 2.

3. An optical storage medium according to claim 1, in which the storage layer essentially consists of one or more compounds of the formula (I) or (II).

4. An optical storage medium according to claim 3, in which the storage layer consists essentially of one compound of the formula (I) or (II).

5. An optical storage medium according to claim 1, on which optically readable marks of different reflectivity are stored.

6. An optical storage medium according to claim 5, in which n and n' are each a number 1 or 2 and A and A' are unsubstituted or monosubstituted phenyl, pyridyl, pyrrolyl, imidazolyl, furyl or thienyl.

7. An optical storage medium according to claim 6, in which the compound is of formula (I), n and n' are each 2, and A and A' are each unsubstituted phenyl.

8. A device for the optical writing, modification or erasing of data in the form of marks of different reflectivity by successive targeting of a monochromatic light beam onto various sites of an optical storage medium according to claim 7, characterized in that the marks of different reflectivity are generated using only continuous laser radiation or only modulated laser radiation.

9. A device for the optical writing, modification or erasing of data in the form of marks of different reflectivity by successive targeting of a monochromatic light beam onto various sites of an optical storage medium according to claim 6, characterized in that the marks of different reflectivity are generated using only continuous laser radiation or only modulated laser radiation.

10. An optical storage medium according to claim 1, in which n and n' are each a number 1 or 2 and A and A' are unsubstituted or monosubstituted phenyl, pyridyl, pyrrolyl, imidazolyl, furyl or thienyl.

11. An optical storage medium according to claim 10, in which the compound is of formula (I), n and n' are each 2, and A and A' are each unsubstituted phenyl.

12. A device for the optical writing, modification or erasing of data in the form of marks of different reflectivity by successive targeting of a monochromatic light beam onto various sites of an optical storage medium according to claim 1, characterized in that the marks of different reflectivity are generated using only continuous laser radiation or only modulated laser radiation.

13. The process for converting a compound of the formula (I) or (II) according to claim 1 from a form having a higher $k_{650}$ value into a form having a lower $k_{650}$ value by applying a mechanical force.

14. An optical storage medium comprising a substrate, a storage layer and a reflective layer, wherein the storage layer comprises a compound of the formula (I)

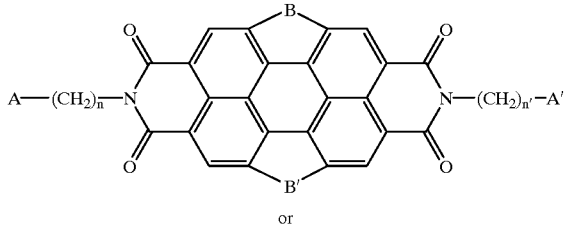

or (II)

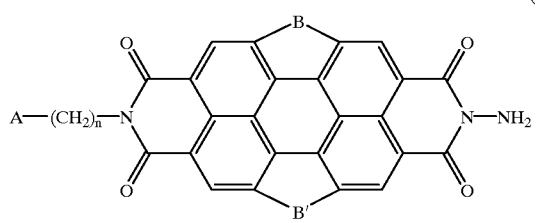

in which A and A', independently of one another, are unsubstituted or mono- or di-halo-, -hydroxy-, —$C_1$–$C_6$alkyl-, —$C_1$–$C_6$alkoxy-, -cyano- or -nitro-substituted phenyl, pyridyl, pyrrolyl, imidazolyl, furyl or thienyl, which can, if desired, be fused to a benzene ring, are halide, tetrafluoroborate or unsubstituted or with one or more halogen substituted $C_1$–$C_6$alkanesulfonate, benzenesulfonate, $C_1$–$C_6$alkylbenzenesulfonate, $C_1$–$C_6$alkylsulfate or di-$C_1$–$C_6$alkyl-phosphonate of N—$C_1$–$C_6$alkyl-pyridiniumyl, or are unsubstituted or mono- or di-hydroxy-substituted $C_2$–$C_6$alkyl or $C_2$–$C_6$alkenyl, whose chain may be uninterrupted or interrupted by one or two oxygen atoms, B and B', independently of one another, are 2 H, S, $S_2$ or $SO_2$, and n and n', independently of one another, are each a number from 1 to 4.

15. An optical storage medium according to claim 14, wherein the substrate is transparent and the storage layer is between the substrate and the reflective layer.

16. An optical storage medium according to claim 1, 15, in which n and n' are both the number 2.

17. An identity or security card comprising an optical storage medium according to claim 1, 2, 14 or 15.

18. A compound of the formula (I) or (II)

(I)

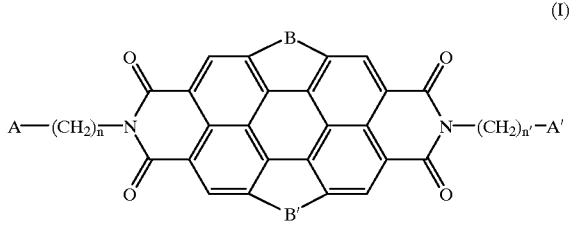

-continued (II)

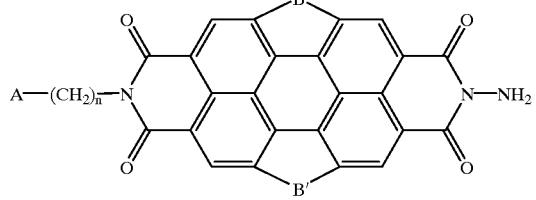

in which A and A', independently of one another, are unsubstituted or mono- or di-halo-, -hydroxy-, —$C_1$–$C_6$alkyl-, —$C_1$–$C_6$alkoxy-, -cyano- or -nitro-substituted phenyl, pyridyl, pyrrolyl, imidazolyl, furyl or thienyl, which can, if desired, be fused to a benzene ring, are halide, tetrafluoroborate or unsubstituted or with one or more halogen substituted $C_1$–$C_6$alkane-sulfonate, benzenesulfonate, $C_1$–$C_6$alkylbenzenesulfonate, $C_1$–$C_6$alkylsulfate or di-$C_1$–$C_6$alkyl-phosphonate of N—$C_1$–$C_6$alkyl-pyridiniumyl, or are unsubstituted or mono- or di-hydroxy-substituted $C_2$–$C_6$alkyl or $C_2$–$C_6$alkenyl, whose chain may be uninterrupted or interrupted by one or two oxygen atoms, B and B', independently of one another, are 2 H, S, $S_2$ or $SO_2$, and n and n', independently of one another, are each a number from 1 to 4 with the provisos that when the compound of the formula (I) or (II) is a compound of the formula (I) wherein B and B' are each 2H, —$(CH_2)_n$—A and —$(CH_2)_{n'}$—A' are not both benzyl, 3'-fluoro-benzyl, 3'-chloro-benzyl, 3'-methoxy-benzyl, 2-phenyl-ethyl, 2-(3'-chloro-phenyl)-ethyl, 2-(3'-methyl-phenyl)-ethyl, 2-(4'-methyl-phenyl)-ethyl, 2-(4'-methoxy-phenyl)-ethyl or unsubstituted$C_1$–$C_6$ alkyl, when the compound of the formula (I) or (II) is a compound of the formula (I) wherein B is S and B' is 2 H or$S_2$, —$(CH_2)_n$—A and —$(CH_2)_{n'}$—A' are not both independently selected from the group consisting of alkyl, substituted aryl, substituted alkyl, alkoxy, aryl alkyl, aryloxy or 2-(2-pyridyl)ethyl), and when the compound of formula (I) or (II) is a compound of formula (II) wherein B and B' are each 2H, —$(CH_2)_n$—A and —$(CH_2)_{n'}$—A' are not both 3'-methoxy-benzyl or 4'-methoxybenzyl.

19. A compound according to claim 18, in which A and A' are pyridyl or halide, tetrafluoroborate or unsubstituted or with one or more halogen substituted $C_1$–$C_6$alkane-sulfonate, benzenesulfonate, $C_1$–$C_6$alkylbenzenesulfonate, $C_1$–$C_6$alkylsulfate or di-$C_1$–$C_6$alkyl-phosphonate of N—$C_1$–$C_6$alkyl-pyridiniumyl.

20. A compound according to claim 18, in which A and A' are unsubstituted or mono- or di-hydroxy-substituted $C_2$–$C_6$alkyl or $C_2$–$C_6$alkenyl, whose chain may be uninterrupted or interrupted by one or two oxygen atoms.

21. A process for the optical writing or reading of data by successive targeting of a monochromatic light beam onto various sites of a substantially not electrically charged storage layer which can be modified thereby, wherein the storage layer comprises a compound of the formula (I) or (II)

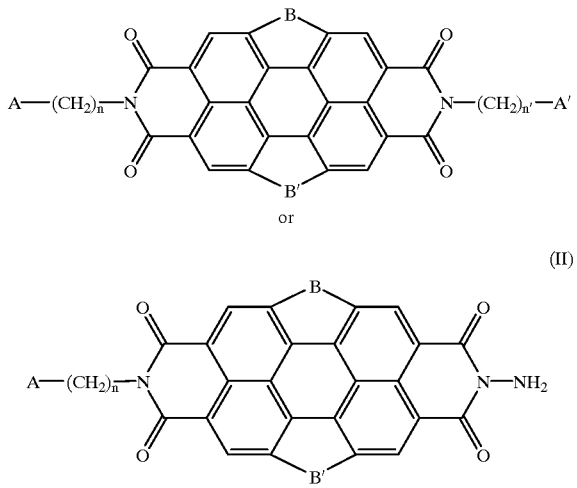

(I)

or (II)

in which A and A', independently of one another, are unsubstituted or mono- or di-halo-, -hydroxy-, —$C_1$–$C_6$akyl-, —$C_1$–$C_6$alkoxy-, -cyano- or -nitro- substituted phenyl, pyridyl, pyrrolyl, imidazolyl, furyl or thienyl, which can, if desired, be fused to a benzene ring, are halide, tetrafluoroborate or unsubstituted or with one or more halogen substituted $C_1$–$C_r$alkanesulfonate, benzenesulfonate, $C_1$–$C_6$alkylbenzenesulfonate, $C_1$–$C_6$alkylsulfate or di-$C_1$–$C_6$alkyl-phosphonate of N—$C_1$–$C_6$alkyl-pyridiniumyl, or are unsubstituted or mono- or di-hydroxy-substituted $C_2$–$C_6$alkyl or $C_1$–$C_6$alkenyl, whose chain may be uninterrupted or interrupted by one or two oxygen atoms, B and B', independently of one another, are 2 H, S, $S_2$ or $SO_2$, and n and n', independently of one another, are each a number from 1 to 4.

22. A process according to claim 21, in which the writing of a mark is carried out using essentially continuous laser radiation.

23. A process according to claim 22, in which the laser radiation has a radiation energy density of 0.2 to 50 kJ/m².

24. A process according to claim 21, in which the writing or modification of a mark is carried out using modulated laser radiation.

25. A process according to claim 24, in which the laser radiation is modulated with a modulation frequency of from 1 to 50 MHz, with a mark-to-space ratio of from 1:1 to 5:1 and a mean radiation energy density of from 1 to 50 kJ//m².

26. A process according to claim 21, in which the writing or reading is carried out in the wavelength range from 400 to 700 nm.

27. A process according to claim 21, in which the smallest length difference between marks of different storage value is less than 0.25 μm.

28. A process for modifying data written or stored in the form of marks of different reflectivity by successive targeting of a monochromatic light beam onto various sites of a substantially not electrically charged storage layer which can be modified thereby, wherein the storage layer comprises a compound of the formula (I) or (II)

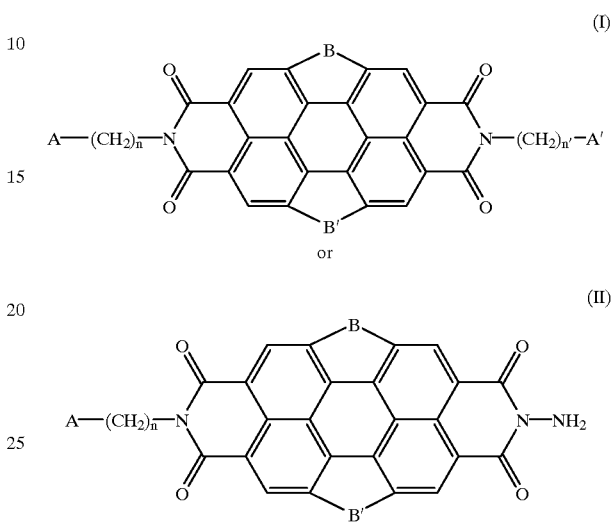

(I)

or (II)

in which A and A', independently of one another, are unsubstituted or mono- or di-halo-, -hydroxy-, —$C_1$–$C_6$alkyl-, —$C_1$–$C_6$alkoxy-, -cyano- or -nitro- substituted phenyl, pyridyl, pyrrolyl, imidazolyl, furyl or thienyl, which can, if desired, be fused to a benzene ring, are halide, tetrafluoroborate or unsubstituted or with one or more halogen substituted $C_1$–$C_6$alkanesulfonate, benzenesulfonate, $C_1$–$C_6$alkylbenzenesulfonate, $C_1$–$C_6$alkylsulfate or di-$C_1$–$C_6$alkyl-phosrhonate of N—$C_1$–$C_6$alkyl-pyridiniumyl, or are unsubstituted or mono- or di-hydroxy-substituted $C_1$–$C_6$alkyl or $C_2$–$C_6$alkenyl, whose chain may be uninterrupted or interrupted by one or two oxygen atoms, B and B', independently of one another, are 2 H, S, $S_2$, or $SO_2$, and n and n', independently of one another, are each a number from 1 to 4.

29. A process according to claim 13, 21 or 28, in which n and n' are each a number 1 or 2 and A and A' are unsubstituted or monosubstituted phenyl, pyridyl, pyrrolyl, imidazolyl, furyl or thienyl.

30. A process according to claim 29, in which the compound is of formula (I), n and n' are each 2, and A and A' are each unsubstituted phenyl.

* * * * *